United States Patent
Chaudhary et al.

(10) Patent No.: US 7,410,801 B2
(45) Date of Patent: Aug. 12, 2008

(54) LAMBDA PHAGE DISPLAY SYSTEM AND THE PROCESS

(75) Inventors: Vijay Kumar Chaudhary, New Delhi (IN); Amita Gupta, New Delhi (IN); Sankar Adhya, Gaithersburg, MD (US); Ira Pastan, Potamac, MD (US)

(73) Assignee: University of Delhi Department of Biochemistry, New Delhi (IN)

( * ) Notice: Subject to any disclaimer, the term of this patent is extended or adjusted under 35 U.S.C. 154(b) by 156 days.

(21) Appl. No.: 10/515,150

(22) PCT Filed: May 20, 2003

(86) PCT No.: PCT/IN03/00193

§ 371 (c)(1),
(2), (4) Date: Nov. 18, 2004

(87) PCT Pub. No.: WO03/096969

PCT Pub. Date: Nov. 27, 2003

(65) Prior Publication Data

US 2005/0181494 A1  Aug. 18, 2005

(30) Foreign Application Priority Data

May 20, 2002 (IN) .............................. 566/DEL/02

(51) Int. Cl.
C12N 15/65 (2006.01)
C12N 15/74 (2006.01)

(52) U.S. Cl. ................. 435/471; 424/184.1; 424/185.1; 424/186.1; 424/187.1; 424/188.1; 424/178.1; 424/277.1; 435/5; 435/6

(58) Field of Classification Search .................... None
See application file for complete search history.

(56) References Cited

U.S. PATENT DOCUMENTS 5,510,099 A  4/1996  Short et al.
5,851,808 A  12/1998  Elledge et al.

OTHER PUBLICATIONS

Hoess RH, Bacteriophage Lambda a a Vehicle for Peptide and Protein Display, Curr Pharma Biotechnol., 2002, 3, 23-28.*

(Continued)

*Primary Examiner*—Bruce Campell
*Assistant Examiner*—Stuart W Snyder
(74) *Attorney, Agent, or Firm*—Hogan & Hartson LLP (57) ABSTRACT

The present invention relates to a process of obtaining recombinant lambdoid bacteriophage with high density display of functional peptides and proteins on surface of said phage comprising of: constructing a donor plasmid having a nucleotide sequence that defines the elements for replication of the vector in bacteria, a selectable marker, a nucleotide sequence flanked by two non-compatible recombination sequences, and an inducible cistron for expression of a capsid protein and a fusion protein; constructing a recipient phage having a nucleotide sequence that defines the lambdoid elements for replication and packaging of the vector into an assembled bacteriophage and encodes an inducible cistron for expression of a selectable marker flanked by two non-compatible recombination sequences; transferring the said donor plasmid to said recipient plasmid to obtain cointegrates; growing said cointegrates in selective liquid medium; harvesting phages displaying protein encoded by the foreign DNA encapsulated in said harvested phage particle.

7 Claims, 9 Drawing Sheets

OTHER PUBLICATIONS

Parmley SF and Smith GP, Antibody-selectable filamentous fd phage vectors: affinity purification of target genes. Gene vol. 73, Issue 2, Dec. 20, 1988, pp. 305-318.*

Sternberg N and RH Hoess. Display of peptides and proteins on the surgace of bacteriophage lambda. PNAS vol. 92, pp. 1609-1613 (1995).*

Siegel, RW et al. Using an in vivo phagemid system to identify non-compatible IoxP sequences. FEBS Lett 499 (2001) 147-153.*

Bethke B and B Sauer. Segmental fenomic replacement by Cre-mediated recombination: genotoxic stress activation of the p53 promoter in single-copy transformants. Nucleic Acids Res. (1997) 25(14):2828-2834.*

Gupta, A et al. High-density Functional Display of Proteins on Bacteriophage Lambda. J Mol Biol. (2003) 334:241-254.*

Peng, et al Acquisition of expressed sequence tags from Schistosoma japonicum cercariae (mainland China strain) and its homology analysis. Di Yi Jun Ui Da Xue Bao. 2001;21(11):809-811.*

Short, et al. Lambda Zap: a bacteriophage lambda expression vector with in vivo excision properties. Nucleic Acids Res. 1988;16:7583-7599.*

Tsuzuki and Rancourt Embryonic stem cell gene targeting using bacteriophage lamdba vectors generated by phage-plasmid recombination. Nucleic Acids Res. 1998;26(4):988-993.*

Sternberg, et al. "Display of peptides and proteins on the surface of bacteriophage λ"; Genetics; Proc. Natl. Acad. Sci. USA; Feb. 1995; pp. 1609-1613; vol. 92.

* cited by examiner (A)

(B)

(C)

```
                      SPACER
LOX P_wt    ATAACTTCGTATA ATGTATGC TATACGAAGTTAT
            TATTGAAGCATAT TACATACG ATATGCTTCAATA
                              *
LOXP511     ATAACTTCGTATA ATGTATAC TATACGAAGTTAT
            TATTGAAGCATAT TACATATG ATATGCTTCAATA
```

| | PROTEIN | Mol. wt (kDa) of Fusion protein | Length of displayed peptide |
|---|---|---|---|
| Dp24cmyc | D \| p24 \| cmyc | 39.0 | 232 aa |
| Dp246cmyc | D \| p246 \| cmyc | 31.0 | 156 aa |
| Dp241cmyc | D \| p241 \| cmyc | 22.0 | 72 aa |
| Dcmyc | D \| MCS \| cmyc | 15.0 | 10 aa |
| p24cmycg8p | p24 \| cmyc \| g8p | 33.1 | 232 aa |
| p246cmycg8p | p246 \| cmyc \| g8p | 24.8 | 156 aa |
| p241cmycg8p | p241 \| cmyc \| g8p | 15.5 | 72 aa |
| p24cmycg3p | p24 \| cmyc \| g3p | 70.1 | 232 aa |
| p246cmycg3p | p246 \| cmyc \| g3p | 61.8 | 156 aa |
| p241cmycg3p | p241 \| cmyc \| g3p | 52.5 | 72 aa |

DISPLAY DENSITY ON λ PHAGES AND M13 PHAGES

| Molecule displayed | Fusion to g8p of M13 | Fusion to g3p of M13 | Fusion to d of λ |
|---|---|---|---|
| p241 (72 amino acids) | 3.5 | 1.4 | 350 |
| p246 (156 amino acids) | 1.7 | 0.8 | 210 |
| p24 (231 amino acids) | 0.5 | 0.7 | 154 |

Calculated based on documentation of Western blots using purified GSTcmyc (Glutathione S-transferase) as control

LAMBDA PHAGE DISPLAY SYSTEM AND THE PROCESS

FIELD OF INVENTON

This invention relates to a process of obtaining recombinant lambdoid bacteriophage and the resultant novel phage display system.

BACKGROUND OF INVENTION

Identification of specific binding sequences is an integral part of research; delineation of antibody recognition sites, study of host-pathogen interaction, elucidation of signal transduction pathways, understanding of cellular responses, all these involve interaction of various macromolecules with one another; most of these interactions occurring between proteins or of a protein with another macromolecule.

For several years, expression libraries have been used for isolating ligands of desired specificity. However, the cumbersome technique of immobilizing expressed proteins on filters and screening large number of filters to obtain one specific binder is labour intensive and exhaustive, limiting the library size and number of clones that can be screened.

It was the concept of phage display introduced by Smith in 1985 (Smith, 1985), which revolutionized the field of proteomics. Large libraries came to be made in phage, and specific binders could be enriched from a milieu of millions under user-defined conditions. DNA encoding the selected molecule present inside the displaying phage particle could then be sequenced to know the identity of the binder. It was this beauty of the phage display system that led to an upsurge in the use of this technology in almost every field of science and unraveling of a plethora of applications, which are increasing everyday. Not limited to phage today, display of peptides/proteins on surface of bacteria, yeast and eukaryotic cells has also come into use.

The filamentous bacteriophage M13, with which was introduced the concept of display system is to date the most widely used system for display of peptides/proteins. Fusion to the minor coat protein, gIIIp and major coat protein, gVIIIp have beep used for display of a range of molecules of different sizes and structure (McCafferty et al., 1990; Scott and Smith, 1990; Kang et al., 1991). Simple biology, ease of culturing and isolating phages, small genome allowing easy manipulations, well documented protocols have all contributed to the immense popularity of the M13 system.

However, M13 morphogenesis occurs in the periplasm, therefore, it is essential that the molecules to be displayed be secretion competent. Though, versions of M13 which allow C-terminal display (Crameri and Blaser, 1996), have been developed, M13 continues to be used primarily as an N-terminal display system. Therefore, it is not useful for studying interactions involving free-C-terminus of display partner and for making full-length cDNA libraries from polyA mRNA.

One system, which obviates these problems associated with M13 display, is lambda display system. Phage lambda assembles in host cytosol and can be used for both N- and C-terminal display of molecules. There have been few papers in recent years that have described display of peptides/proteins on phage lambda as fusion to the capsid protein 'd' and tail protein 'v' (Dunn, 1995; Sternberg and Hoess, 1995; Mikawa et al., 1996). However, this system has not gained much popularity, which can be attributed to several reasons including the fact that
(i) the lambda phage biology is more complex than of M13 phage. Unlike M13 which grows by extruding from host cell, lambda can follow a lysogenic or lytic mode; therefore manipulation of lambda life cycle is more difficult,
(ii) lambda genome is very large (50 kb), therefore isolation of viral DNA, insertion of user defined restriction sites, cloning of foreign fragments and then packaging of the ligated product in vitro to make lambda particles is difficult and the library sizes achieved are less than those obtained with phage/phagemid based M13 vectors.

SUMMARY OF THE INVENTION

Accordingly the instant invention describes a phage lambda display system which allows high efficiency cloning in phage lambda using lox-cre recombination system and high density display of protein/peptides fused to the head protein, 'd', of phage lambda. Further, the display of different molecules on phage lambda is compared with display of same molecules on phage M13.

The instant invention provides for a novel system for C-terminal display on phage lambda that avoids cloning into lambda phage DNA. This C-terminal display system achieves cloning efficiencies comparable to those obtained with any plasmid system and eliminates the step of in vitro packaging of phage lambda. The high-density display of foreign proteins is useful in studying low affinity protein-protein interactions, which is more efficient as compared to M13 display system.

The object of the instant invention is to provide a system for obtaining recombinant lambdoid bacteriophage with high-density display of functional peptides and proteins that has high efficiency cloning in phage lambda.

Another object is to provide a method for detecting the presence of insert-encoded polypeptide in a given sample.

Yet another object is to create a library of cointegrates and maintain the same library size in the lambda genome as obtained during cloning in the donor plasmid.

Another object of the instant invention is to provide a method for identification of the insert-encoded polypeptide by sequencing the insert DNA in the cointegrate.

Accordingly the instant invention provides for a process of obtaining recombinant lambdoid bacteriophage with high density display of functional peptides and proteins on surface of said phage comprising of:
  constructing a donor plasmid having a nucleotide sequence that defines the elements for replication of the vector in bacteria, a selectable marker, a nucleotide sequence flanked by two non-compatible recombination sequences, and an inducible cistron for expression of a capsid protein and a fusion protein.
  constructing a recipient phage having a nucleotide sequence that defines the lambdoid elements for replication and packaging of the vector into an assembled bacteriophage and encodes an inducible cistron for expression of a selectable marker flanked by two non-compatible recombination sequences,
  transferring the said donor plasmid to said recipient plasmid to obtain cointegrates
  growing said cointegrates in selective liquid medium
  harvesting phages displaying protein encoded by the foreign DNA encapsulated in said harvested phage. particle.

The instant invention also provides for a library of cointegrate containing recombinant phage particles wherein each particle contains a recombinant lambdoid bacteriophage vector comprising the donor plasmid vector integrated into recipient phage genome.

Further the instant invention also provides for a method for detecting the presence of insert-encoded polypeptide in a sample.

The instant invention also provides for a method for producing more copies of the selected recombinant phage particles.

The said invention provides for a method for identification of the insert-coded polypeptide by sequencing the insert DNA in the said cointegrate.

A novel donor plasmid.
A novel recipient phage
A novel DCO (double crossover) cointegrate.

BRIEF DESCRIPTION OF THE DRAWINGS

FIG. 9 shows the binding of lambda phages displaying a single chain Fv (scFv)

DETAILED DESCRIPTION OF THE DRAWINGS

FIG. 1(A) shows the diagrammatic representation of donor plasmid pVCDcDL1. The diagram shows only relevant genes. The backbone is derived from pUC119 and shows Lac PO, Lac Promoter—operator; $Amp^r$, β lactamase gene, F ori, original of replication derived from filamentous bacteriophage; $LoxP_{wt}$, wild type Lox P site, $LoxP_{511}$, mutant Lox P site, D, DNA encoding gpD of bacteriophage Lambda, collagenase, sequence cleaved by enzyme collagenase, MCS (multiple cloning site); tag, a 10 amino acid sequence from cmyc that is recognised by Mab, 9E10.

FIG. 1(B) shows the diagrammatic representation of recipient bacteriophage Lambda, λDL1. The diagram shows a DNA cassette containing complete transcription and translation unit of lacZα flanked by $LoxP_{wt}$ (Wild type LoxP). $LoxP_{511}$, (mutant LoxP) has been inserted in the unique Xba I site; $D_{am}$ is the D gene of Lambda with amber mutation.

Figure 1:
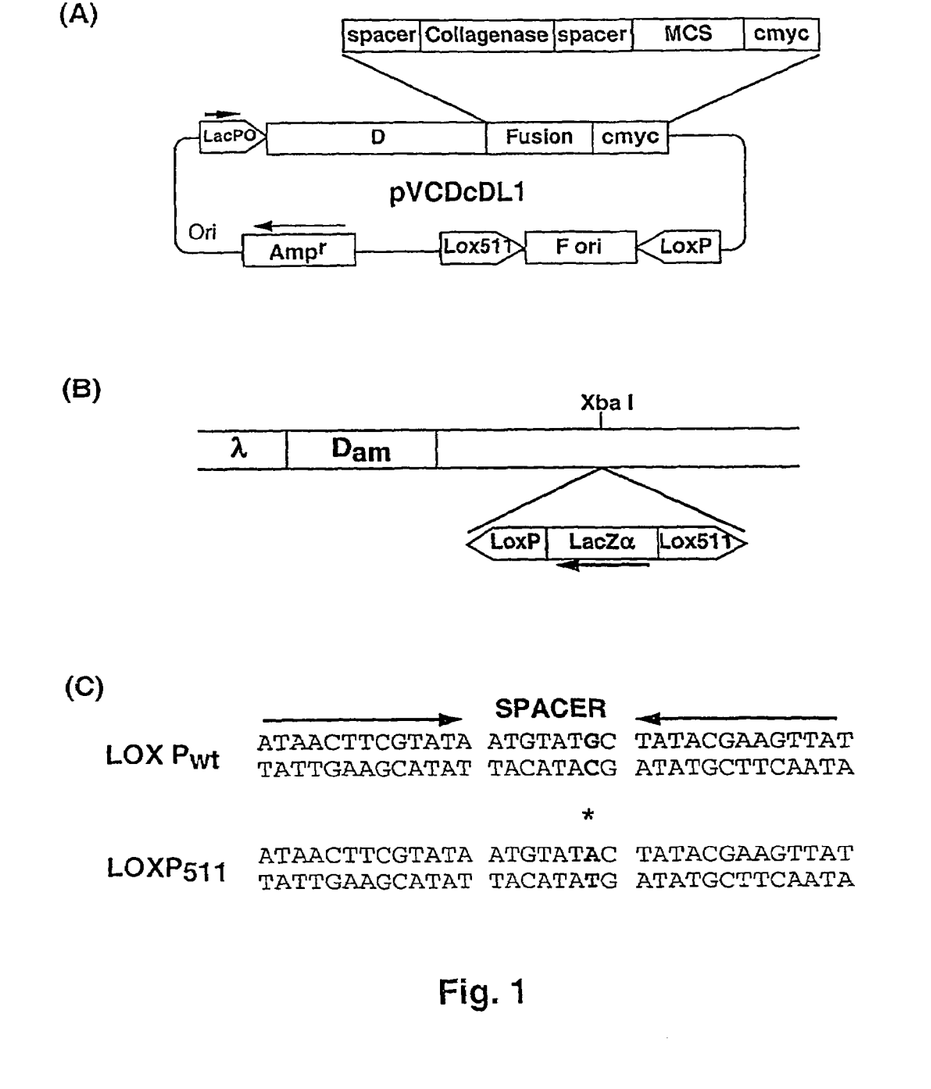
FIG. 1(A) shows a diagrammatic representation of donor plasmid, pVCDcDL1.
FIG. 1(B) shows the diagrammatic representation of recipient bacteriophage Lambda, λDL1.
FIG. 1(C) shows sequences of lox $P_{wt}$ and lox $P_{511}$ sites are shown. The difference between lox $P_{wt}$ and lox $P_{511}$ is shown in bold letters.

Fig 1(C) shows sequences of $LoxP_{wt}$ and $LoxP_{511}$ site. The difference between $LoxP_{wt}$ and $LoxP_{511}$ is shown in bold letters. The sequences shown in FIG. 1 (C) are SEQ ID NO:1 (ATAACTTCGT ATAATGTATG CTATACGAAG TTAT), SEQ ID NO:2 (ATAACTTCGT ATAGCATACA TTATAC-GAAG TTAT). SEQ ID NO:3 (ATAACTTCGT ATAATG-TATA CTATACGAAG TTAT). and SEQ ID NO:4 (ATAACT-TCGT ATAGTATACA TTATACGAAG TTAT).

Figure 2:
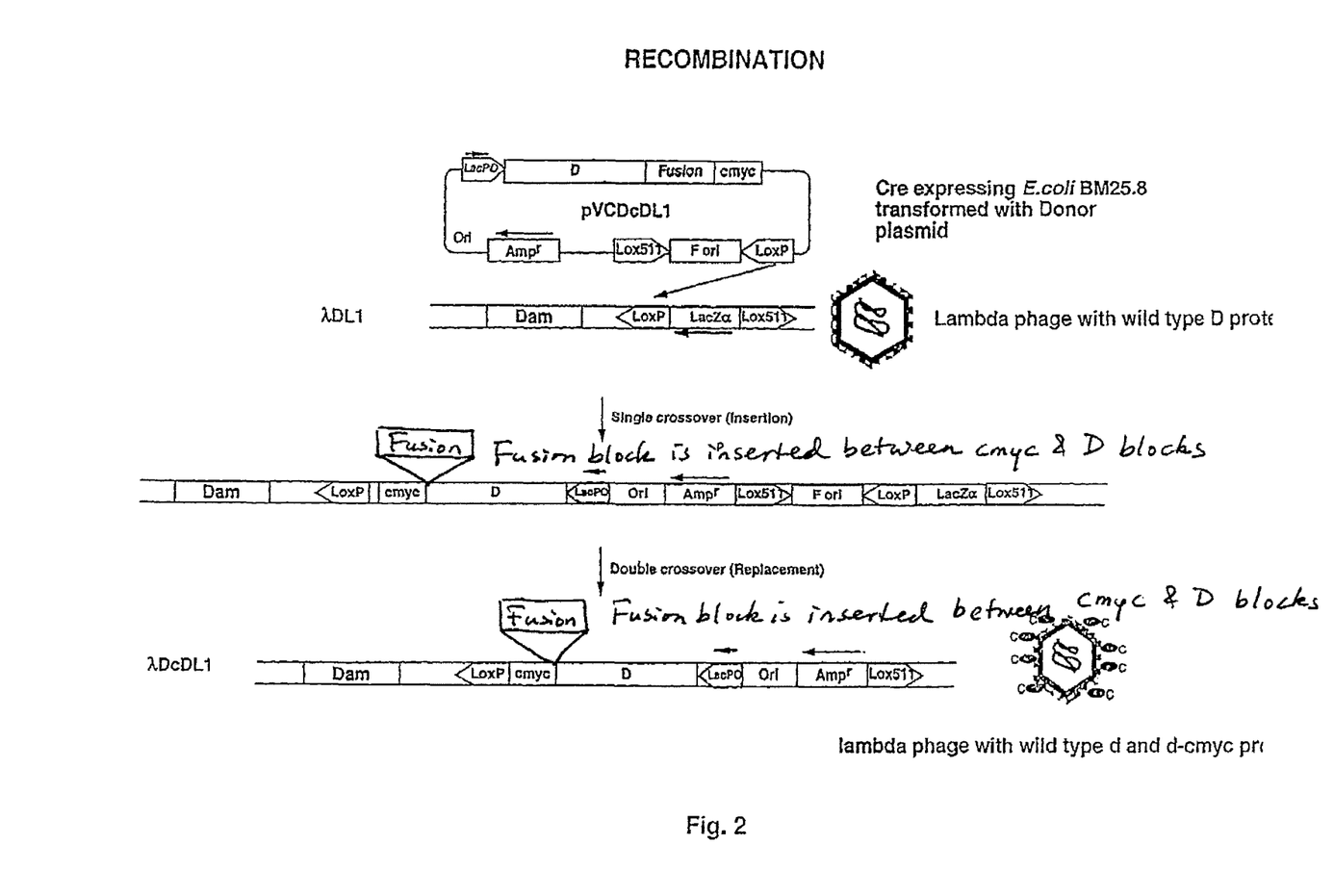
FIG. 2 shows the diagrammatic representation of recipient bacteriophage Lambda, λDL1

FIG. 2 shows the process of recombination. The donor plasmid e.g. pVDcDL1 is transformed in Cre expressing E. coli strain, BM 25.8. The culture of transformants is infected with recipient bacteriophage λDL1, which does not display any protein fused to gpD. Single cross over (SCO) or double cross over (DCO) event takes places and integration of plasmid confers Ampicillin resistance. The $Amp^r$ clones are grown to produce bacteriophage lambda displaying desired protein fused to gpD. Description of various gene segments is given in FIG. 1.

Figure 3:
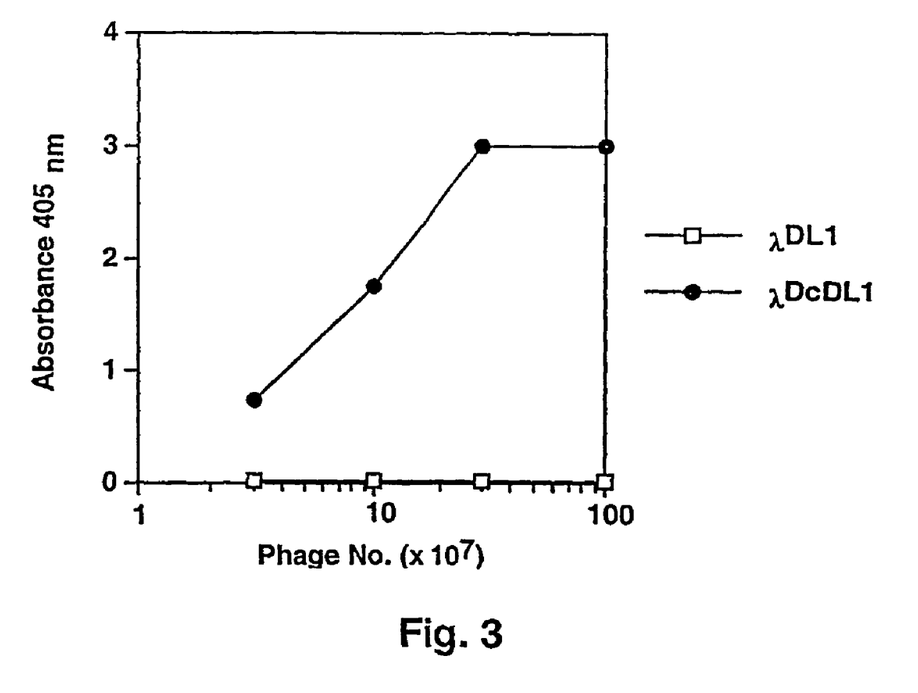
FIG. 3 shows ELISA reactivity of lambda phages displaying cmyc peptide

FIG. 3 shows the binding of λDcDL1 phages to Mab 9E10. The microtitre ELISA plates were coated with Mab 9E10 (100 microlitre/well of 1:1000 dilution of ascitic fluid). Indicated number of purified phages were added and incubated for 1 hr at 37° C. The bound phages were detected by adding Rabbit anti-λ polyclonal serum followed by HRP-conjugated Goat anti-Rabbit IgG (H+L).

Figure 4:
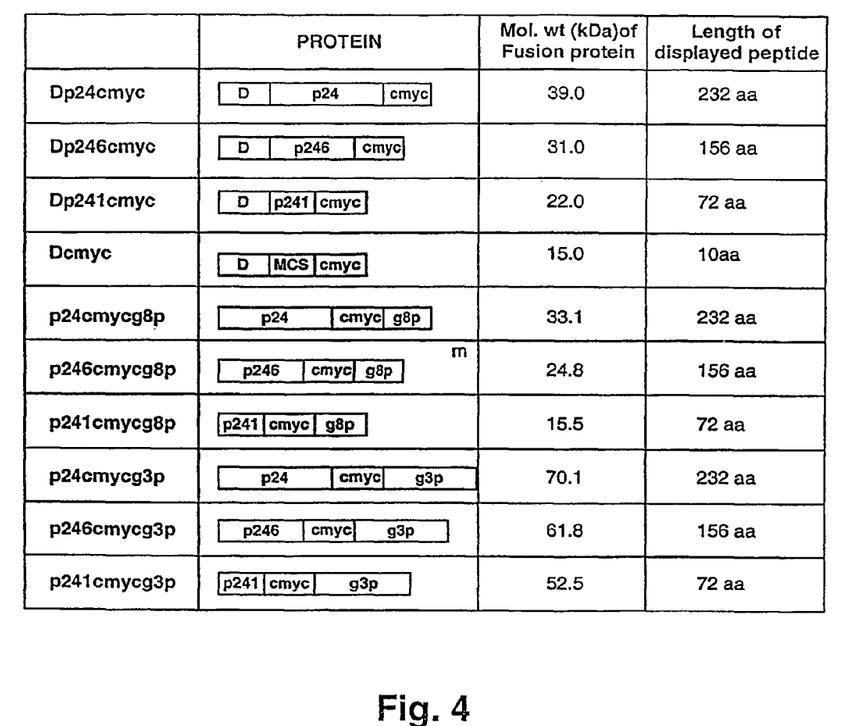
FIG. 4 shows the diagrammatic representation of various peptides fused to coat proteins of bacteriophage M13 and λ.

FIG. 4 shows the diagrammatic representation of various peptides fused to coat proteins of bacteriophage M13 and Lambda. These peptides are p24, HIV-1 capsid protein p24 of 231 amino acids; p246, amino acids 1 to 156 of HIV-1 p24; p241, amino acids 1 to 72 of HIV-1 p24. D, protein gpD of bacteriophage lambda; g8p, gene 8 protein of phage M13; g3p, gene 3 protein of phage M13; cmyc, a 10 amino acid peptide tag recognized by MAb 9E10. The tabulated data also shows the molecular weights of fusion proteins displayed on phage surface along with length of displayed p24 sequence.

Figure 5:
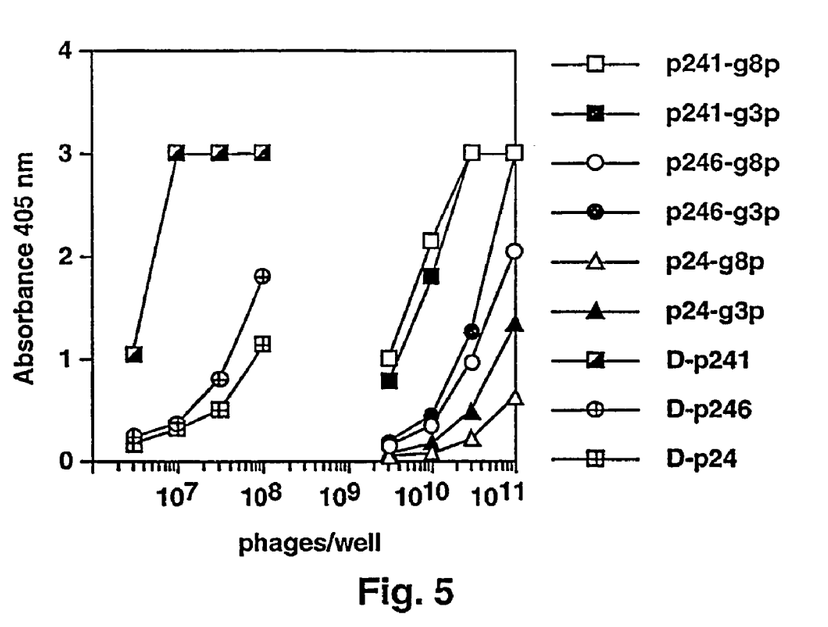
FIG. 5 shows the comparison of ELISA reactivity of various phages displaying p24 and its fragments

FIG. 5 is a comparative chart depicting the comparison of ELISA reactivity of various phages displaying p24 and its fragments. Microtitre ELISA plates were coated with MAb H23 (1:1000 dilution of ascitic fluid). Different dilutions of phages were incubated for 1 hr at 37° C. The bound phages were detected by addition of Rabbit anti-M13 or Rabbit anti-Lambda polyclonal sera followed by HRP conjugated Goat anti-Rabbit IgG (H+L). p24-g8p, M13 phages displaying fusion protein between 1-72 amino acids of HIV-1 p24 fused at the N-terminus of g8p; p241-g3p, same as p241-g8p but with fusion at the N-terminus of g3p; p246-g8p, M13 phages displaying protein between 1-156 amino acids of HIV-1 p24 fused at the N-terminus of g8p; p246-g3p, same as p246-g8p but with fusion at the N-terminus of g3p; p24-g8p, M13 phage displaying HIV-1 p24 (amino acids 1-231) fused at the N-terminus of g8p; p24-g3p, same as p24-g8p but with fusion at the N-terminus of g3p; D-p241, lambda phages displaying fusion protein of 1-72 amino acids of HIV-1 p24 at the C-terminus of gpD; D-p246; same as D-p241 but containing 1-156 amino acids of HIV-1 p24; D-p24, same as D-p241 but containing full length p24 (amino acids 1-231).

Figure 6:
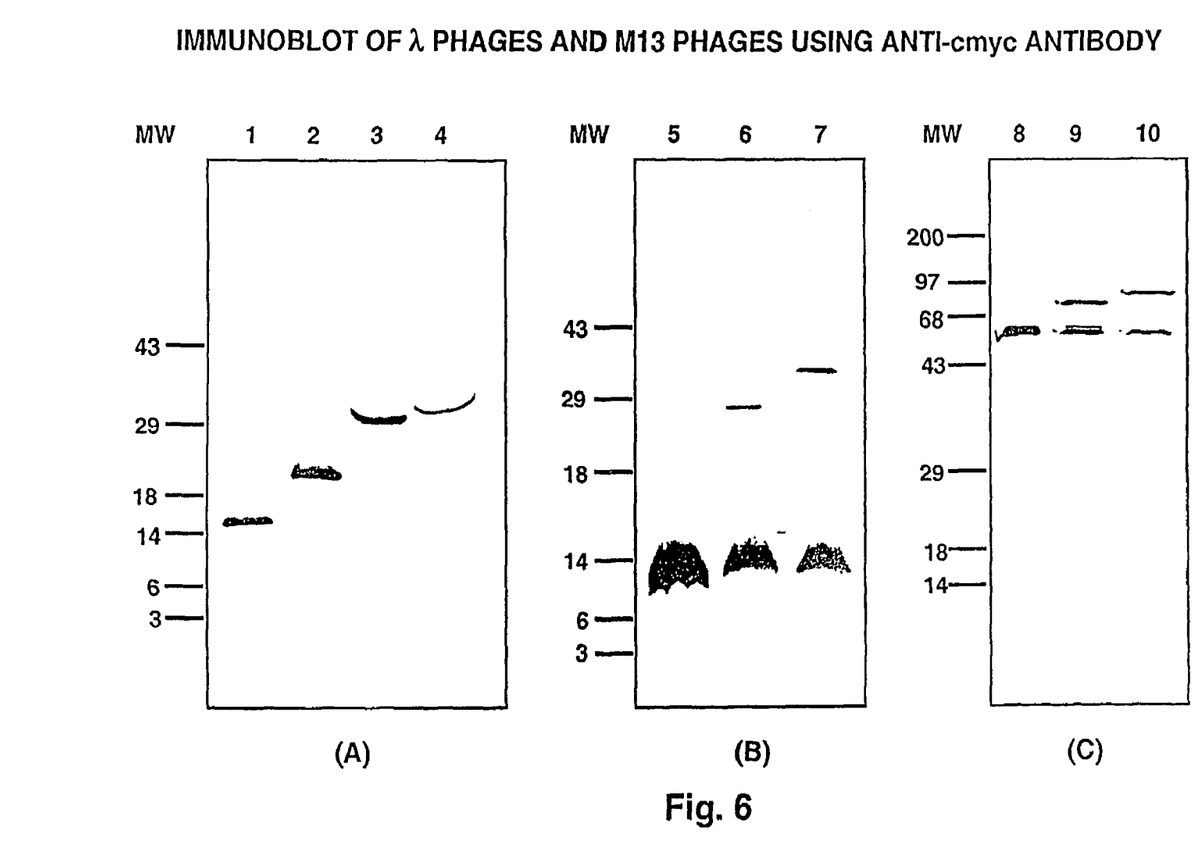
FIG. 6 shows the Western blot analysis of M13 and lambda phages displaying HIV-1 p24 and its fragments.

FIG. 6 shows the results of the Western blot analysis of M13 and lambda phages displaying HIV-1 p24 and its fragments. Purified phages were subjected to SDS-PAGE at indicated acrylamide concentration under reducing conditions. After transferring on to PVDF membrane, the blots were probed with anti-cmyc MAb 9E10 followed by HRP-conjugated Goat anti-Mouse IgG (H+L).

A. $1 \times 10^8$ gpD displaying lambda phages on 12.5% PAG;
B. $2 \times 10^{11}$ g8p displaying M13 phages per lane on 12.5% PAG;
C. $1 \times 10^{11}$ g3p displaying M13 phages per lane on 10% PAG; Lane 1 is for lambda phage displaying D-cmyc fusion protein; Lane 2, 5, and 8, are for phages displaying fusion protein of 1-72 amino acid of HIV-p24 (p241) fused to respective phage coat protein; lane 3, 6, and 9 are for phages displaying fusion protein of 1-156 amino acids of HIV-1 p24 (p246) fused to phage coat proteins and lane 4, 7, and 10 are for phages displaying fusion proteins of HIV-1 p24 (231 amino acids) fused with various coat proteins.

Figure 7:
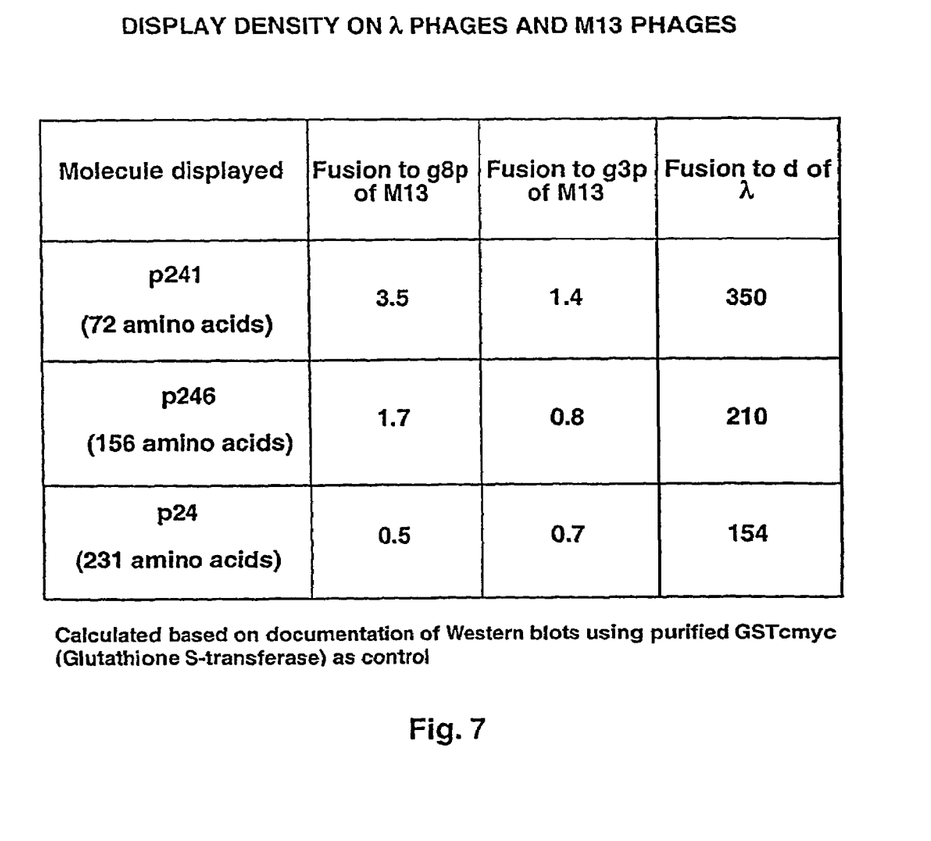
FIG. 7 shows the comparison of display density on Lambda and M13 phages

FIG. 7 shows the tabulated data comparing the display density on Lambda and M13 phages. Western blots as shown in FIG. 6 were subjected to densitometric scanning. Calculation of number of displayed fusion proteins per phage particle was made by estimating the number of molecules in the band corresponding to the fusion protein in comparison to known amount of purified GST-cmyc analysed on the same blot.

Figure 8:
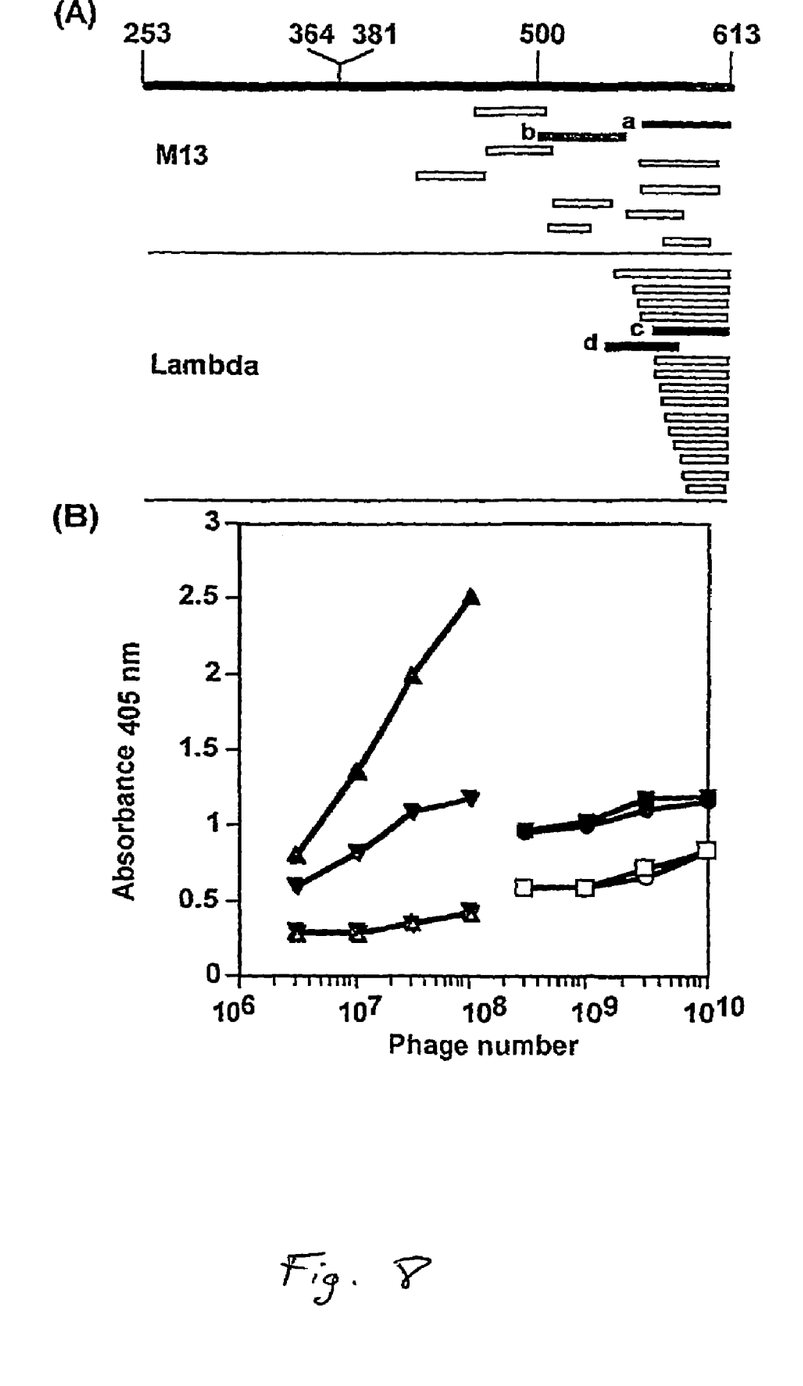
FIG. 8A shows the alignment of inserts in the selected phage
FIG. 8B shows the reactivity of phages in ELISA

FIG. 8. A shows the alignment of inserts in phage selected after panning of PE gene-fragment library in M13 and λ phage on human serum. Only 15 clones (out of 30 clones) of lambda are shown. Solid line represents PE-38 and the numbers above the line denote amino acid position in the full length PE. The clones selected for ELISA (Panel B) are indicated as 'a' to 'd'.

FIG. 8B ELISA showing reactivity of phages displaying PE fragments. Reactivity of M13 phage, clone a and b and lambda phage, clone c and d to pre-treatment (open symbols) and post-treatment (filled symbols) samples.

FIG. 9 depicts the binding of Lambda phages displaying a single chain Fv (scFv). Microtitre ELISA plates were coated with mesothelin (100 microgram/well). Indicated number of purified λDcSS1DL1 phages displaying SS1scFv, λDcDL1 (control phage) displaying cmyc peptide and λDL1 (control phage) displaying no peptide were added. The bound phages were detected by adding Rabbit anti—λ polyclonal serum followed by HRP-conjugated Goat anti-Rabbit IgG (H+L).

DETAILED DESCRIPTION OF THE INVENTION WITH REFERENCE TO THE Accompanying Drawings The described system for display on phage lambda utilizes high-efficiency plasmid based cloning protocols followed by in vivo recombination process for cloning of desired DNA in lambda genome. In this system, the DNA encoding molecule to be displayed is cloned in a donor plasmid using conventional cloning protocols. Cre expressing bacteria are then transformed with this donor plasmid. When the transformed cells are infected with recipient lambda particles, the donor plasmid undergoes Cre mediated recombination with lambda DNA at the Lox sites and gets integrated into the lambda genome.

This λ cointegrate formed by recombination expresses d-fusion protein (FIG. 2). When lambda morphogenesis occurs and phage assembly takes place, the λ cointegrate DNA gets packaged in pre-formed head and the D-fusion protein gets incorporated in the newly formed phage capsid. The progeny particles therefore give ampicillin resistant transductants (allowing easy selection) and display D-fusion protein.

The use of in vivo recombination process for transferring DNA from plasmid into the lambda genome maintains the library size obtained during cloning in donor plasmid.

The invention shall now be described with the help of some examples:

EXAMPLE 1

The system described above is optimized using donor plasmid pVCDcDL1, which expresses D protein fused to a ten amino acid tag, cmyc. pVCDcDL1 was used to transform BM25.8 (Cre+) cells and the transformants were infected with recipient lambda, λDL1. The lysate obtained after culture growth and lysis was plated to obtain ampicillin resistant transductants. These transductants were analysed by PCR to check for integration of plasmid into λ DNA.

Two kinds of cointegrates were obtained. Single crossover at one of the lox sites resulted in formation of SCO (single crossover cointegrates) which contained the entire donor plasmid and lacZα cassette (FIG. 2). A second crossover event resulted in excision off ori and lacZα cassette and this was called DCO (double crossover cointegrates). Both SCO and DCO produced same number of phages and the display of D-cmyc fusion protein was comparable.

DcDL1 phages were made and tested for display of D-cmyc in ELISA. Purified DcDL1 phages were added to microtitre wells coated with anti-cmyc antibody, 9E10. DL1 phages were used as Control.

DcDL1 phages showed dose-dependent binding to 9E10, (as seen in FIG. 3) showing that they displayed D-cmyc fusion protein. No binding was observed with DL1 phages that do not display D-cmyc fusion protein.

To study the display of different size molecules as d-fusion protein on lambda, we cloned different length fragments of HIV-1 capsid protein, p24 in pVCDcDL1. The recombinants were named pVCDc(p241)DL1, pVCDc(p246)DL1 and pVCDc(p24)DL1. The three constructs were then used to transform host BM25.8 and recombination was carried out to obtain Dc(p241)DL1, Dc(p246)DL1 and Dc(p24)DL1.

These phages were purified and characterized for reactivity to anti-p24 antibody in ELISA and for display density by Western blot. Also, the same fragments of p24 were also cloned in M13 g3p and g8p display vectors for a comparative study.

FIG. 4 shows the various fragments displayed along with their molecular weight. In ELISA, p24 displaying and M13 phages were captured on wells coated with anti-p24 Mab, H23 and then bound phages were detected using anti-phage polyclonal sera. For all the three fragments displayed, phages showed better reactivity, 2-3 orders of magnitude more than the corresponding M13 (g8p and g3p display) phages (FIG. 5). To quantitate the number of displayed molecules per phage particle, Western blot analysis was done. Known number of purified phages were electrophoresed on SDS-PAG and transferred to PVDF membrane and probed with anti-cmyc Mab, 9E10 (FIG. 6). Purified GSTcmyc (Glutathione S-transferase fused to cmyc) was used as control to quantitate the bands obtained. The results are shown in FIG. 7. Lambda phages were found to display several folds more amount of protein than M13 phages. As seen in FIG. 7, lambda was found to display 100 times more copies of p241 compared to $g^8p$ and g3p display phages. The difference was greater with larger size fragments, p246 and p24.

These results clearly show that for all fragment sizes, the display density on lambda is 2-3 orders of magnitude more than on M13. This system will be useful in studying weak interactions and in epitope mapping where high-density display is advantageous.

M13 assembly occurs in the periplasm of the cell. The oxidising environment of the periplasm allows formation of disulfide binds in the displayed molecules. Lambda assembles in the cytosol and therefore, disulfide bonded molecules may not be displayed in functional form on lambda.

To check this, we displayed single chain fragment (scFv) of an anti-mesothelin antibody, SS1 as D-fusion protein on lambda. DcSS1DL1 was checked for functional display of scFv in ELISA. DcSS1DL1 phages were added to mesothelin coated wells and captured phages were detected using anti-phage polyclonal sera. As shown in FIG. 8, DcSS1DL1 phages showed specific binding to mesothelin, indicating that the displayed scFv was functional. No binding was observed with DL1 and DcDL1 phages. This shows that disulfide containing peptides and proteins can be displayed in functional form on lambda phage.

EXAMPLE 2

The 'Donor' plasmid vector pVCDcDL1, (FIG. 1A) a high copy number vector based on pUC119, was constructed for cloning sequences to be displayed as d-fusion protein on. This plasmid vector contains 'd' gene of under lacPO followed by a Gly-Ser spacer, collagenase cleavage site, multiple cloning site (MCS) and a decapeptide tag, cmyc. Cloning of DNA sequences in the MCS allows formation of d-fusion protein with the fusion protein present at C-terminus of d protein. The collagenase site allows cleavage of the fusion partner from d protein and is used for elution of bound phages after panning by collagenase treatment. The cmyc tag allows easy identification of the fusion protein. The vector contains M13 phage origin of replication (f ori), flanked by Lox $P^{wt}$ and Lox $P_{511}$ sites (Hoess et al., 1982).

This cassette is extremely stable and there is no loss of 'f ori' sequence upon repeated cycles of growth (more than five times) in $Cre^+/Cre^-$ host (data not shown).

pVCDcDL1 was analysed for the expression of d-cmyc protein. It was found that ~50% of total cellular protein in TG1 cells on IPTG induction was d-cmyc fusion protein. Localization experiments showed that all the expressed protein was present in soluble fraction of cell cytoplasm (data not shown).

For preparing the recipient 'lambda' vector a sequence coding for lacZ and flanked by lox sites (FIG. 1C), was cloned in unique Xba I site of Dam (Stemberg and Hoess, 1995). This vector was named DL1 (FIG. 1B). This vector has 'd' gene carrying amber (TAG) codon.

In vivo recombination of DL-1 and pVCDcDL1 produced cointegrates displaying fusion protein.

BM 25.8 ($Cre^+$) cells were transformed with plasmid pVCDcDL1 and grown to O.D. ~0.3 in LB $Amp_{100}$ (LB medium containing 100 g/ml of ampicillin). The cells from 1 ml culture were harvested and resuspended in 100 Iof DL-1 phage at an MOI of 1.0. After incubation at 37° C. for 10 minutes, the sample was diluted in 1 ml LB $Amp_{100}$ $MgCl_2$ (10 mM), IPTG (1 mM) and grown at 37° C. with shaking till lysis occured (~3-4 hours). The cell-free supernatant was titrated on TG1 ($Cre^-$) cells and $Amp^r$ colonies obtained were analysed by PCR using specific primers L1 and L4 to identify lambda cointegrates, DcDL1.

$Amp^r$ colonies of cointegrate were grown in LB $Amp_{100}$ and the supernatant containing phages was titrated to obtain plaques. 0.1 ml TG1 cells were infected with a single plaque and then diluted in 5 ml LB and the culture was grown at 37° C. for 3-4 hours or till lysis was observed. $CHCl_3$ was then added (final concentration 1%) to complete lysis and the cell-free supernatant was titrated to determine phage numbers.

For large-scale purification of phages, 15 ml TG1 cells were infected with phages at MOI of 0.01, diluted to one litre in LB medium and grown at 37° C. till lysis occured. The cell-free supernatant was then treated with DNase/RNase. PEG-NaCl was added to a final concentration of 10% PEG/ 1M NaCl and kept a 4° C. for 4 hrs. The phages were harvested by centrifugation at 20,000×g for 30 minutes and then suspended in 10 mM Tris containing MgCl2 and 0.1% gelatin (TMG). The phage suspension was then subjected to ultra centrifugation at 50,000 rpm (70 Ti) for 3 hours. The phage pellet was suspended in TMG and re-centrifuged at 50,000 rpm. The pellet was then suspended in TMG and phage suspension was titrated for pfu (plaque forming units).

EXAMPLE 3

Comparison of Lambda Display System with M13 Display System

DNA sequences encoding different length fragments of HIV capsid protein p24 were amplified from pVCp24210 (Gupta et al., 2000) using 5' primer which annealed to first eight codons of the fragment and contained Nhe I site and 3' primer which annealed to last eight codons of the fragment and contained Mlu I site. The amplified products were digested with Nhe I and Mlu I and cloned in Nhe I-Mlu I digested, dephosphorylated vector, pVCDcDL1 to create pVCDc(p241)DL1, pVCDc(p246)DL1 and pVCDc(p24) DL1.

The three constructs were then used to transform $Cre^+$ host BM25.8 and recombination was carried out to obtain Dc(p241)DL1, Dc(p246)DL1 and Dc(p24)DL1.

DNA encoding different p24 fragments were cloned as Nhe I-Mlu I inserts into gIII display vector, pVC3TA726 (Sampath et al., 1997) and similar gVIII display vector, pVCp2418426 (VKC, personal communication). The recombinants pVC(p241)3426, pVC(p246)3426 and pVC(p24) 3426 (displaying p241, p246 and p24 as gIIIp fusion) and pVC(p241)18426, pVC(p246)18426 and pVC(p24)18426 (displaying p241, p246 and p24 as gVIIIp fusion) were grown and phage particles were made after infection with helper phage, VCSM13. The phages were precipitated with PEG-NaCl and purified by ultracentrifugation. The purified phages were then titrated as $Amp^r$ transductants cfu (colony forming units).

Ultra-purified phages were used for western blot analysis. Phages were mixed with 2× Lamelli buffer containing ME and electrophoresed on 10% SDS-12.5% PAG/10% PAG. The samples were then transferred onto PVDF membrane (immobilon, Millipore) and probed with 1:1000 dilution of anti-cmyc MAb, 9E10/anti-p24 MAb, H23 followed by 1:2500 dilution of HRP conjugated Goat anti-Mouse IgG (H+L).

For ELISA, microtitre wells were coated with 1:1000 dilution of MAb 9E10 or H23 and ultra-purified phages were added to the coated wells. The bound phages were detected with Rabbit anti-polyclonal serum or Rabbit anti-M13 polyclonal serum followed by HRP conjugated Goat anti-Rabbit IgG (H+L). Construction of *Pseudomonas* Exotoxin (PE) Gene-fragment Library in λ and M13 Vectors. Fifty-200 bp random fragments of DNA encoding PE-38, a 38 KDa fragment of P E Debinski and Pastan, 1992 were produced by Dnase I digestion and ligated as blunt-ended fragments in pVCDcDL3 using previously described protocols Gupta et al., 2001. The ligation mix was electroporated into BM25.8 cells and plated on two 150 mm LBAmpGlu (LBAmp medium containing 1% Glucose) plates on to obtain $5×10^6$ independent clones. The transformants were scrapped and suspension stored at –70° C. Cells ($1×10^9$) of the library were grown in 10 ml LBAmpGlu to an $OD_{600}$ of 0.3, harvested and suspended in 1 ml of λDL1 phage lysate at an MOI of 1.0. After incubation at 37° C. for 10 min, the samples were diluted in 10 ml LBAmp containing MgCl2 (10 mM) and grown at 37° C. with shaking for 3 h until cell lysis. The cell-free supernatant pfu (10 ml) was used to infect an exponential phase culture of TG1 cells (10 ml) and plated on twenty 150 mm LBAmpGlu plates. The $Amp^r$ colonies obtained were scraped and stored at –70° C. Cells ($1×10^9$) harbouring cointegrates were diluted into 50 ml of LBAmp medium and grown at 37° C. for 8 h to produce phage. The cell-free supernatant was directly used for affinity selection.

PE-derived fragments were also ligated to Sma I digested gIIIp based phagemid display vector, pVCEPI13426 Gupta et al., 1999 to obtain gene-fragment library in M13. A library size of $6 \times 10^6$ independent clones was obtained in TG1 cells and was used to produce phage as described previously Kushwaha et al., 1994.

EXAMPLE 4

Affinity Selection of Binders by Bio-Panning.

For bio-panning, wells of microtiter plates were coated with 1:1000 dilution of ascitic fluid of anti-cmyc MAb 9E10 and phage lysate was added to the coated wells Gupta et al., 1999. The captured λ phages were eluted with Collagenase. 1 unit of Collagenase was added to each well and incubated for 30 min at RT. The eluted phages were serially diluted and used to infect TG1 cells and plated to determine phage infected cells as pfu and cfu. For M13 library, the captured phage were eluted using low pH buffer Gupta et al., 1999 and titrated on TG1 as cfu. For panning of PE gene-fragment library on MAb, wells were first coated with goat anti-mouse IgG followed by 1:100 dilution of anti-PE MAb culture supernatant (Test wells) or buffer (Control wells). For panning of this library on human serum, wells were coated with Goat anti-human (IgG+IgM) followed by 1:100 dilution of serum from patients treated with PE-based immunotoxins (Test wells) or pre-treatment serum of patients (Control wells). Phage lysate was added to each well, incubated at 37° C. for hr and unbound phages were removed by washing as described previously (b). Individual Amp$^r$ colonies were grown and phage particles were produced as described previously Kushwaha et al., 1994. The cell-free supernatants were used for ELISA.

Cell-free supernatants of individual phage clones selected in bio-panning experiments were tested in ELISA. For this, wells were coated with 1:1000 dilution of rabbit anti-λ polyclonal serum or rabbit anti-M13 polyclonal serum and phage were added to the coated wells. After removing unbound phage, 1:100 dilution of anti-PE MAb (culture supernatant) or serum from patients treated with PE-based immunotoxins was added. The bound phage were detected with HRP conjugated goat anti-mouse IgG (H+L)/HRP conjugated goat anti-human (IgG+IgM).

EXAMPLE 5

Display of Antibody Fragments on Phage Lambda

DNA encoding scFv fragment of anti-mesothelin antibody, SS1 (Chowdhury and Pastan, 1999) was amplified from pVNLSS11346 and cloned as Nhe I-Mlu I insert in pVCDcDL1, to obtain pVCDcSS1DL1. BM25.8 cells were transformed with pVCDcSS1DL1 and recombination was performed using DL1 as described above to form DcSS1DL1. These phages were purified using protocol described above for DcDL1.

ELISA was performed to check functionality of displayed scFv. For this, microtitre wells were coated with 100 ng of mesothelin and ultra-purified phages were added to the coated wells. The bound phages were detected with Rabbit anti polyclonal serum followed by HRP conjugated Goat anti-Rabbit IgG (H+L).

The described system for display on phage lambda utilises high-efficiency plasmid based cloning protocols followed by in vivo recombination process for cloning of desired DNA in lambda genome. In this system, the DNA encoding molecule to be displayed is cloned in a donor plasmid using conventional cloning protocols. Cre expressing bacteria are then transformed with this donor plasmid. When the transformed cells are infected with recipient lambda particles, the donor plasmid undergoes Cre mediated recombination with lambda DNA at the Lox sites and gets integrated into the lambda genome. This cointegrate formed by recombination expresses d-fusion protein (FIG. 2). When lambda morphogenesis occurs and phage assembly takes place, the cointegrate DNA gets packaged in pre-formed head and the D-fusion protein gets incorporated in the newly formed phage capsid. The progeny particles therefore give ampicillin resistant transductants (allowing easy selection) and display D-fusion protein. The use of in vivo recombination process for transferring DNA from plasmid into the lambda genome maintains the library size obtained during cloning in donor plasmid.

This system was optimised by using donor plasmid pVCDcDL1, which expresses D protein fused to a ten amino acid tag, cmyc. pVCDcDL1 was used to transform BM25.8 (Cre+) cells and the transformants were infected with recipient lambda, DL1. The lysate obtained after culture growth and lysis was plated to obtain ampicillin resistant transductants. These transductants were analysed by PCR to check for integration of plasmid into DNA. Two kinds of cointegrates were obtained. Single crossover at one of the lox sites resulted in formation of SCO (Single crossover cointegrates) which contained the entire donor plasmid and lacZ cassette (FIG. 2). A second crossover event resulted in excision of f ori and lacZ cassette and this was called DCO (double crossover cointegrates). Both SCO and DCO produced same number of phages and the display of D-cmyc fusion protein was comparable. DcDL1 phages were made and tested for display of D-cmyc in ELISA. Purified DcDL1 phages were added to microtitre wells coated with anti-cmyc antibody, 9E10. DL1 phages were used as Control. As shown in FIG. 3, DcDL1 phages showed dose-dependent binding to 9E10, showing that they displayed D-cmyc fusion protein. No binding was observed with DL1 phages that do not display D-cmyc fusion protein.

To study the display of different size molecules as d-fusion protein on lambda, different length fragments of HIV-1 capsid protein, p24 were cloned in pVCDcDL1. The recombinants were named pVCDc(p241)DL1, pVCDc(p246)DL1 and pVCDc(p24)DL1. The three constructs were then used to transform host BM25.8 and recombination was carried out to obtain Dc(p241)DL1, Dc(p246)DL1 and Dc(p24)DL1. These phages were purified and characterised for reactivity to anti-p24 antibody in ELISA and for display density by Western blot. Also, the same fragments of p24 were also cloned in M13 g3p and g8p display vectors for a comparative study. FIG. 4 shows the various fragments displayed along with their molecular weight. In ELISA, p24 displaying and M13 phages were captured on wells coated with anti-p24 Mab, H23 and then bound phages were detected using anti-phage polyclonal sera. For all the three fragments displayed, phages showed better reactivity, 2-3 orders of magnitude more than the corressponding M13 (g8p and g3p display) phages (FIG. 5). To quantitate the number of displayed molecules per phage particle, Western blot analysis was done. Known number of purified phages were electrophoresed on SDS-PAG and transferred to PVDF membrane and probed with anti-cmyc Mab, 9E10 (FIG. 6). Purified GSTcmyc (Glutathione S-transferase fused to cmyc) was used as control to quantitate the bands obtained. The results are shown in FIG. 7. Lambda phages were found to display several folds more amount of protein than M13 phages. As seen in FIG. 7, lambda was found to display 100 times more copies of p241 compared to g8p and g3p display phages. The difference was greater with larger size fragments, p246 and p24.

These results clearly show that for all fragment sizes, the display density on lambda is 2-3 orders of magnitude more than on M13. This system will be useful in studying weak interactions and in epitope mapping where high-density display is advantageous.

EXAMPLE 6

High Density Display Leads to Efficient Selection in Bio-panning.

The utility of high density display on λ in epitope mapping was evaluated using gene-fragment library of PE carrying fragments ranging in size from 50-200 bp and encoding peptides as fusion to gpD of λ or the gIIIp of M13. These libraries were first used to map the epitope recognised by a MAb against PE in bio-panning. The binding of lambda library phages was 2000 times more than the binding to uncoated wells, while with M13 library this ratio was only 10 times indicating high specific binding of lambda phages (Table 1). Sequence analysis of individual phage from MAb-coated wells revealed that 88% of the analysed λ clones displayed a fragment of PE on their surface, as compared to 63% M13 clones.

This difference could be either due to more selective and specific binding of λ phage or due to the fact that C-terminal display in λ allows three times more functional display as compared to the N-terminal display in M13 system. Lambda clones displaying a PE fragment produced high dose-dependent reactivity in ELISA to anti-PE MAb, while none of the M13 clones showed any significant reactivity despite the addition of 1000-fold more M13 phage (data not shown). These results clearly show that the number of peptides displayed on λ phage was several orders of magnitude higher than on M13 phage, corroborating our earlier results obtained with p24 displaying phage.

Anti-toxin antibodies are one of the major bottle-neck in the way of successful use of immunotoxins for cancer therapy as repeated treatment with immunotoxin is not possible. Therefore, identification of immunodominant epitopes followed by mutagenesis, might produce toxin molecules which would exhibit full bio efficacy, but will not elicit neutralizing antibodies.

Therefore, the library was used to identify immunodominant regions of PE against which antibodies are present in the serum of human patients after treatment with recombinant immunotoxins containing PE-38 Pai et al., 1991. Microtiter wells were coated with pre-treatment (control) and post-treatment (test) pooled sera from patients, and panning was done.

As shown in Table 2, 90% of the selected λ clones in test sample were in frame with gpD and displayed a fragment of PE, while in the case of M13 phage only 16% clones were in frame with gIIIp suggesting specific enrichment in case of lambda phage. Alignment of sequence showed that the majority of the λ clones aligned to the last 50 amino acids of PE whereas in the case of M13, only a few clones aligned to this region (FIG. 3A). A second round of panning with the amplified elute of first panning of M13 phage did not result in any increase in the number of clones with alignment to any one region of PE (data not shown). This difference between λ clones and M13 clones could be due to low ligand concentration per phage particle in case of M13. In ELISA, the lambda clones showed high reactivity with post-treatment serum pool and gave low reactivity with pre-treatment serum pool (FIG. 3B). M13 phage showed reactivity with pre-treatment serum pool with only marginal increase in reactivity with post-treatment serum pool. The difference in ELISA reactivity between λ phage and M13 phage was 2-3 orders of magnitude, again establishing the importance of high density of display on λ phage.

M13 assembly occurs in the periplasm of the cell. The oxidising environment of the periplasm allows formation of disulfide binds in the displayed molecules. Lambda assembles in the cytosol and therefore, disulfide bonded molecules may not be displayed in functional form on lambda. To check this, we displayed single chain fragment (scFv) of an anti-mesothelin antibody, SS1 as D-fusion protein on lambda. DcSS1DL1 was checked for functional display of scFv in ELISA. DcSS1DL1 phages were added to mesothelin coated wells and captured phages were detected using anti-phage polyclonal sera. As shown in FIG. 9, DcSS1DL1 phages showed specific binding to mesothelin, indicating that the displayed scFv was functional. No binding was observed with DL1 and DcDL1 phages. This shows that disulfide containing peptides and proteins can be displayed in functional form on lambda phage.

TABLE 1

Panning of λ and M13 Library on Anti-PE MAb

|  | λ library | | M13 library | |
| --- | --- | --- | --- | --- |
|  | Test | Control | Test | Control |
| Input phages | $1 \times 10^8$ | $1 \times 10^8$ | $1 \times 10^{10}$ | $1 \times 10^{10}$ |
| Output phages | $1 \times 10^4$ | 5 | $9 \times 10^5$ | $9 \times 10^4$ |
| Fold enrichment* | $2 \times 10^3$ |  | 10 |  |
| Clones displaying PE fragment % (No. positive/No. analyzed)† | 88% (22/25) |  | 63% (23/36) |  |
| Clones ELISA reactive % (No. positive/No. analyzed)555 | 100% (12/12) |  | 0% (0/14) |  |

*Fold enrichment = output phage in test/output phage in Control.
†The inserts in clones from test well selected after panning were sequenced to check for reading frame and display of PE fragment.
555 The clones displaying PE fragments were analysed for binding to anti-PE MAb in ELISA.

TABLE 2

Panning of λ and M13 Library on Human Serum

|  | λ library | | M13 library | |
| --- | --- | --- | --- | --- |
|  | Control | Test | Control | Test |
| Input phage | $1 \times 10^8$ | $1 \times 10^8$ | $1 \times 10^{10}$ | $1 \times 10^{10}$ |
| Output phage | $1 \times 10^3$ | $2 \times 10^4$ | $6 \times 10^4$ | $7 \times 10^6$ |
| Fold enrichment* | 20 | | 123 | |
| Clones displaying PE fragment % (No. positive/No. analyzed)† | 25% (8/30) | 90% (30/33) | 9% (3/34) | 15.7% (11/70) |

Control refers to pre-treatment serum and test refers to post-treatment serum of patients * and † as in Table 1

While particular embodiments of the present invention have been described above, the present invention also pertains to novel donor plasmid as mentioned in any of the claims filed herewith. In addition, the present invention further pertains to novel recipient phage as mentioned in any of the claims filed herewith. Also, the present invention yet further pertains to novel DCO cointeg rate as mentioned in any of the claims filed herein.

REFERENCES

Chowdhury, P. S. and Pastan, I. (1999) Improving antibody affinity by mimicking somatic hypermutation in vitro. Nat Biotechnol 17, 568-572.

Crameri, R. and Blaser, K. (1996) Cloning *Aspergillus fumigatus* allergens by the pjuFo filamentous phage display system. Int Arch Allergy Immunol 110, 41-45.

Debinski, W. and Pastan, I. (1992) Monovalent immunotoxin containing truncated form of *Pseudomonas* exotoxin as potent antitumor agent. Cancer Res 52, 5379-5385.

Dunn, I. S. (1995) Assembly of functional bacteriophage lambda virions incorporating C-terminal peptide or protein fusions with the major tail protein. J Mol Biol 248, 497-506.

Gupta, S., Arora, K., Gupta, A. and Chaudhary, V. K. (2000) Gag-Derived Proteins of HIV-1 Isolates from Indian Patients: Cloning, Expression, and Purification of p24 of B- and C-Subtypes. Protein Expr Purif 19, 321-328.

Gupta, S., Arora, K., Sampath, A., Khurana, S., Singh, S. S., Gupta, A. and Chaudhary, V. K. (1999) Simplified gene-fragment phage display system for epitope mapping. Biotechniques 27, 328-330,332-324.

Gupta, S., Arora, K., Sampath, A., Singh, S. S., Gupta, A. and Chaudhary, V. K. (2001) Mapping of hiv-1 Gag epitopes recognized by polyclonal antibodies using gene-fragment phage display system. Prep Biochem Biotechnol 31, 185-200.

Hoess, R. H., Ziese, M. and Sternberg, N. (1982) P1 site-specific recombination: nucleotide sequence of the recombining sites. Proc Natl Acad Sci USA 79, 3398-3402.

Kang, A. S., Barbas, C. F., Janda, K. D., Benkovic, S. J. and Lerner, R. A. (1991) Linkage of recognition and replication functions by assembling combinatorial antibody Fab libraries along phage surfaces. Proc Natl Acad Sci USA 88, 4363-4366.

Kushwaha, A., Chowdhury, P. S., Arora, K., Abrol, S. and Chaudhary, V. K. (1994) Construction and characterization of M13 bacteriophages displaying functional IgG-binding domains of staphylococcal protein A. Gene 151, 45-51.

McCafferty, J., Griffiths, A. D., Winter, G. and Chiswell, D. J. (1990) Phage antibodies: filamentous phage displaying antibody variable domains. Nature 348, 552-554.

Mikawa, Y. G., Maruyama, I. N. and Brenner, S. (1996) Surface display of proteins on bacteriophage lambda heads. J Mol Biol 262, 21-30.

Pai, L. H., Bookman, M. A., Ozols, R. F., Young, R. C., Smith, J. W., 2nd, Longo, D. L., Gould, B., Frankel, A., McClay, E. F., Howell, S. and et al. (1991) Clinical evaluation of intraperitoneal *Pseudomonas* exotoxin immunoconjugate OVB3-PE in patients with ovarian cancer. J Clin Oncol 9, 2095-2103.

Sampath, A., Abrol, S. and Chaudhary, V. K. (1997) Versatile vectors for direct cloning and ligation-independent cloning of PCR-amplified fragments for surface display on filamentous bacteriophages. Gene 190, 5-10.

Scott, J. K. and Smith, G. P. (1990) Searching for peptide ligands with an epitope library. Science 249, 386-390.

Smith, G. P. (1985) Filamentous fusion phage: novel expression vectors that display cloned antigens on the virion surface. Science 228, 1315-1317.

Sternberg, N. and Hoess, R. H. (1995) Display of peptides and proteins on the surface of bacteriophage lambda. Proc Natl Acad Sci USA 92, 1609-1613.

---

We claim:

1. A process of obtaining recombinant lambdoid bacteriophage with high density display of functional peptides and proteins on surface of said bacteriophage comprising the steps of:
   a) Constructing a donor plasmid comprising:
      A first recombination sequence, and
      a second recombination sequence, wherein said first and second recombination sequences are incompatible with each other, and wherein said first and second recombination sequences flank
      a nucleotide sequence that defines the elements for replication of the vector in bacteria,
      a nucleotide sequence encoding a first selectable marker, and
      a first inducible cistron comprising:
         a promoter for transcribing said first cistron,
         a first ribosome binding site,
         a first translatable nucleotide sequence encoding a lambdoid bacteriophage capsid polypeptide
         a second translatable sequence operatively linked to said first translatable sequence and encoding a first linker polypeptide, a protease cleavable peptide sequence, a second linker polypeptide, and
         a sequence adapted for ligation of an insert polynucleotide or an MCS;
      wherein each translatable nucleotide sequence is in the same reading frame such that induction of said first cistron expresses a fusion polypeptide consisting of said capsid polypeptide, linker polypeptide, protease cleavage site, linker polypeptide, and said MCS-encoded or said insert-encoded polypeptide;
      nucleotide sequence comprising:
         lambdoid replication and packaging elements,
         said first recombination sequence, and
         said second recombination sequence, wherein said first and second recombination sequences flank
      a second inducible cistron for expression of a second selectable marker transferring the polynucleotide sequences located between said
         first and second recombination sequences of said donor plasmid to said
         recipient phage to obtain cointegrates;
   d) propagating said cointegrates in liquid medium selective for said first selectable marker; and
   e) harvesting phages displaying said fusion polypeptide.

2. A process of obtaining recombinant lambdoid bacteriophage with high density display of functional peptides and proteins on surface of said bacteriophage comprising the steps of:
   a) Constructing a donor plasmid comprising:
      A first recombination sequence, and
      a second recombination sequence, wherein said first and second recombination sequences are incompatible with each other, and wherein said first and second recombination sequences flank
      a nucleotide sequence that defines the elements for replication of the plasmid in bacteria,
      a nucleotide sequence encoding a first selectable marker, and
      a first inducible cistron comprising a lambdoid capsid/exogenous protein fusion protein encoding sequence) constructing a recipient phage having a nucleotide sequence comprising:
         lambdoid replication and packaging elements,
         said first recombination sequence, and
         said second recombination sequence, wherein said first and second recombination sequences flank
         a second inducible cistron for expression of a second selectable marker;
   c) transferring the polynucleotide sequences located between said first and second recombination sequences of said donor plasmid to said recipient phage to obtain cointegrates;
   d) propagating said cointegrates in liquid medium selective for said first selectable marker; and
   e) harvesting phages displaying said fusion protein,
   wherein said plasmid has the same genetic map as shown in FIG. 2 for pVCDcDL1.

3. A process of obtaining recombinant lambdoid bacteriophage with high density display of functional peptides and proteins on surface of said bacteriophage comprising the steps of:
   a) Constructing a donor plasmid comprising:
      A first recombination sequence, and
      a second recombination sequence, wherein said first and second recombination sequences are incompatible with each other, and wherein said first and second recombination sequences flank
      a nucleotide sequence that defines the elements for replication of the plasmid in bacteria,
      a nucleotide sequence encoding a first selectable marker, and
      a first inducible cistron comprising a lambdoid capsid/heterologous polypeptide fusion protein encoding sequence;

b) constructing a recipient phage having a nucleotide sequence comprising:
  lambdoid replication and packaging elements,
  said first recombination sequence, and
  said second recombination sequence, wherein said first and second recombination sequences flank
  a second inducible cistron for expression of a second selectable marker;
c) transferring the polynucleotide sequences located between said first and second recombination sequences of said donor plasmid to said recipient phage to obtain cointegrates;
d) propagating said cointegrates in liquid medium selective for said first selectable marker; and
e) harvesting phages displaying said fusion protein,
wherein said cointegrate containing recombinant phage particles comprise a matrix of proteins encapsulating a lambdoid genome encoding said fusion protein,
wherein said fusion protein is surface accessible in said matrix, and
wherein said fusion protein comprises gpD lambdoid bacteriophage capsid polypeptide, a linker polypeptide, a protease cleavage site, a linker poly peptide, and said heterologous polypeptide.

4. A process as claimed in claim 1 wherein said heterologous polypeptide of the cointegrate-containing recombinant phage particles is selected from the group consisting of capsid protein p24 of Human Immunodeficiency Virus, decapeptide cmyc, and a single chain antibody fragment (scFv).

5. A process as claimed in claim 2 wherein said heterologous polypeptide of the cointegrate-containing recombinant phage particles is capsid protein p24 of Human Immunodeficiency Virus.

6. A process as claimed in claim 2 wherein said heterologous polypeptide of the cointegrate-containing recombinant phage particles is decapeptide cmyc.

7. A process of obtaining recombinant lambdoid bacteriophage with high density display of functional peptides and proteins on surface of said bacteriophage comprising the steps of:
a) Constructing a donor plasmid comprising:
  A first recombination sequence, and
  a second recombination sequence, wherein said first and second recombination sequences are incompatible with each other, and wherein said first and second recombination sequences flank
  a nucleotide sequence that defines the elements for replication of the vector in bacteria,
  a nucleotide sequence encoding a first selectable marker, and
  a first inducible cistron comprising a lambdoid capsid/heterologous polypeptide fusion protein encoding sequence;
b) constructing a recipient phage having a nucleotide sequence comprising:
  a lambdoid replication and packaging elements,
  said first recombination sequence, and
  said second recombination sequence, wherein said first and second recombination sequences flank
  a second inducible cistron for expression of a second selectable marker
c) transferring the polynucleotide sequences located between said first and second recombination sequences of said donor plasmid to said recipient phage to obtain cointegrates;
d) propagating said cointegrates in liquid medium selective for said first selectable marker; and
e) harvesting phages displaying said fusion protein,
wherein the number of fusion protein molecules on the surface of each recombinant lambdoid phage particle is 100-1000 fold more than capsid protein molecules on surface of each particle of filamentous phage M13.

* * * * *

SEQUENCE LISTING

```
<160> NUMBER OF SEQ ID NOS: 4

<210> SEQ ID NO 1
<211> LENGTH: 34
<212> TYPE: DNA
<213> ORGANISM: Artificial
<220> FEATURE:
<223> OTHER INFORMATION: Synthetic oligonucleotide

<400> SEQUENCE: 1
ataacttcgt ataatgtatg ctatacgaag ttat                            34

<210> SEQ ID NO 2
<211> LENGTH: 34
<212> TYPE: DNA
<213> ORGANISM: Artificial
<220> FEATURE:
<223> OTHER INFORMATION: Synthetic oligonucleotide

<400> SEQUENCE: 2
ataacttcgt atagcataca ttatacgaag ttat                            34

<210> SEQ ID NO 3
<211> LENGTH: 34
<212> TYPE: DNA
<213> ORGANISM: Artificial
<220> FEATURE:
<223> OTHER INFORMATION: Synthetic oligonucleotide

<400> SEQUENCE: 3
```

```
                                         -continued ataacttcgt ataatgtata ctatacgaag ttat                                34

<210> SEQ ID NO 4
<211> LENGTH: 34
<212> TYPE: DNA
<213> ORGANISM: Artificial
<220> FEATURE:
<223> OTHER INFORMATION: Synthetic oligonucleotide

<400> SEQUENCE: 4
ataacttcgt atagtataca ttatacgaag ttat                                34
```